United States Patent
Manabe et al.

(10) Patent No.: US 8,124,789 B2
(45) Date of Patent: Feb. 28, 2012

(54) METHOD FOR PRODUCING GLYCOSYLATED INDOLE COMPOUND AND ANTIBODY AGAINST THE COMPOUND

(75) Inventors: Shino Manabe, Tokyo (JP); Yukishige Ito, Tokyo (JP); Yoshito Ihara, Wakayama (JP)

(73) Assignee: Riken, Saitama (JP)

( * ) Notice: Subject to any disclaimer, the term of this patent is extended or adjusted under 35 U.S.C. 154(b) by 295 days.

(21) Appl. No.: 12/329,844

(22) Filed: Dec. 8, 2008

(65) Prior Publication Data

US 2010/0028329 A1 Feb. 4, 2010

(30) Foreign Application Priority Data

Dec. 6, 2007 (JP) ................. 2007-315707

(51) Int. Cl.
- *A61K 39/395* (2006.01)
- *C07D 209/20* (2006.01)
- *C07D 403/14* (2006.01)
- *C07K 16/00* (2006.01)

(52) U.S. Cl. .................. 548/497; 424/130.1; 530/387.1; 544/405

(58) Field of Classification Search .................. None
See application file for complete search history.

(56) References Cited

OTHER PUBLICATIONS

Ihara et al., "Increased expression of protein C-mannosylation in the aortic vessels of diabetic Zucker rats," Glycobiology, 2005, vol. 15, No. 4, pp. 383-392.*
Manabe, Shino; Ito, Yukishige "The first synthesis of N-Man-Trp: alternative mannosylation modification of protein," Synlett 2008, No. 6, pp. 880-882; Advanced online publication Feb. 26, 2008.*
Li et al., J. Biol Chem, 2005, 280, 38513-38521.
Nyhammer, T. et al., food. Chem. 1985, 17, 289-296.
Gutsche, B. et al., Biochem. J. 1999, 343, 11-19.
C. Unverzagt et al., Tetrahedron Lett. 2004, 45, 295-297.

* cited by examiner

*Primary Examiner* — Shafiqul Haq
*Assistant Examiner* — Galina Yakovleva
(74) *Attorney, Agent, or Firm* — Greenblum & Bernstein, P.L.C.

(57) ABSTRACT

This invention provides a method of producing a large amount of an α-form or β-form of N-pyranosyl-tryptophan having a specified structure and preparing an antibody therefrom. The method comprises a step of allowing a pyranose compound to react with a 3-pyrazyl-indole compound in the presence of a first base to obtain a 1-pyranosyl-3-pyrazyl-indole compound, and a step of treating the 1-pyranosyl-3-pyrazyl-indole compound with an acid, treating the resultant with a hydrogenation catalyst, and further treating the resultant with a second base to synthesize N-pyranosyl-tryptophan, thereby producing an antibody therefrom.

21 Claims, 3 Drawing Sheets

Fig. 1 i) BuLi, THF, 64%; ii) Mg, EtOH, 98%, iii) KHMDS, THF, 49%, iv) HCl, dioxane, H$_2$O, 71%, v) H$_2$, Pd (OH)/C, AcOH, H$_2$O then LiOH•H$_2$O, H$_2$O, 75%.

METHOD FOR PRODUCING GLYCOSYLATED INDOLE COMPOUND AND ANTIBODY AGAINST THE COMPOUND

BACKGROUND OF THE INVENTION

1. Field of the Invention

The present invention relates to a method for producing N-pyranosyl-tryptophan having a specified structure via organic synthesis. More particularly, the present invention relates to a method for producing N-pyranosyl-tryptophan comprising allowing a pyranose compound having an epoxide group and a protected hydroxyl group to react with a 3-pyrazyl-indole compound and then treating the resulting 1-pyranosyl-3-pyrazyl-indole compound with an acid and a catalyst. Further, the present invention relates to a method for producing an antibody that is specific to N-pyranosyl-tryptophan using N-pyranosyl-tryptophan as a hapten.

2. Description of the Related Art

As a novel modified type of glycoprotein, N-mannosyl tryptophan, in which mannose has been bound to an indole nitrogen atom of tryptophan, was discovered based on a type of peroxidase (Li et al., J. Biol. Chem., 2005, 280, 38513). However, a method for organic synthesis of N-mannosyl tryptophan was not known before now.

Meanwhile, the presence of N-glucosyl-tryptophan has been identified in fruit and Chinese medicine. As a method for producing β-N-glucosyl-tryptophan, a method comprising a step of heating of N-α-acetyl-D-tryptophan and glucose for a long period of time to synthesize the target compound is known (Nyhammer, T. et al., Food. Chem. 1985, 17, 289-296; Gutsche, B. et al., Biochem. J. 1999, 343, 11-19; and C. Unverzagt et al., Tetrahedron Lett. 2004, 45, 295-297). Such method, however, causes a lower yield of β-N-glucosyl-tryptophan synthesized and large amounts of by-products, and thus, makes separation and purification of β-N-glucosyl-tryptophan very difficult. Further, synthesis of a derivative was difficult due to the removal of an acetamide group.

BRIEF SUMMARY OF THE INVENTION

The conformation of N-mannosyl tryptophan at the anomeric position has not yet been elucidated due to quantitative limits, and the biological functions thereof also remain unknown since no useful method of chemical synthesis that can produce a sufficient yield of N-pyranosyl-tryptophan having a strictly specified structure, such as N-mannosyl tryptophan and N-glucosyl-tryptophan, has yet been known. Accordingly, a method for producing large amounts of such compounds has been awaited for the purposes such as investigation of functions of such compounds in vivo.

An object of the present invention is to overcome the problems of conventional techniques described above. Specifically, an object of the present invention is to provide a method for producing a large amount of an α-form or β-form of N-pyranosyl-tryptophan having a specified structure, and particularly an α-form or β-form of N-mannosyl tryptophan. Further, an object of the present invention is to provide a method for producing 1-pyranosyl-3-pyrazyl-indole compounds used for producing a large amount of an α-form or β-form of N-pyranosyl-tryptophan having a specified structure.

Further, an object of the present invention is to provide an antibody against N-pyranosyl-tryptophan, which can contribute to elucidation of biological functions of N-pyranosyl-tryptophan, and a method for producing this antibody.

The present inventors have conducted concentrated studies in order to attain the above objects. As a result, they succeeded in synthesizing N-pyranosyl-tryptophan by allowing a pyranose compound having an epoxide group and a protected hydroxyl group to react with a 3-pyrazyl-indole compound in the presence of a base to obtain a 1-pyranosyl-3-pyrazyl-indole compound and then treating the 1-pyranosyl-3-pyrazyl-indole compound with hydrochloric acid and two or more metal catalysts.

Specifically, the present invention provides a method for producing N-pyranosyl-tryptophan comprising:

a step of allowing a pyranose compound represented by the formula (1):

wherein X each independently represent a hydroxyl-protecting group, to react with a 3-pyrazyl-indole compound represented by the formula (2):

wherein $R_1$, $R_2$, and $R_3$ each independently represent an alkyl group having 1 to 6 carbon atoms, in the presence of a first base to obtain a 1-pyranosyl-3-pyrazyl-indole compound represented by the formula (3):

wherein X each independently represent a hydroxyl-protecting group; and $R_1$, $R_2$, and $R_3$ each independently represent an alkyl group having 1 to 6 carbon atoms; and a step of treating the 1-pyranosyl-3-pyrazyl-indole compound with an acid, treating the resultant with a hydrogenation catalyst, and further treating the resultant with a second base to obtain N-pyranosyl-tryptophan represented by the formula (4):

(4)

According to the method for producing N-pyranosyl-tryptophan of the present invention, preferably, the combination of the pyranose and the pyranosyl is selected from the group consisting of a combination of α-mannose and α-mannosyl, a combination of β-mannose and β-mannosyl, a combination of α-glucose and α-glucosyl, and a combination of β-glucose and β-glucosyl.

According to the method for producing N-pyranosyl-tryptophan of the present invention, preferably, the first base is selected from the group consisting of potassium hexamethyldisilazide (KHMDS), lithium 2,2,6,6-tetramethyl piperizide (LiTMP), lithium diisopropylamide (LDA), lithium hexamethyldisilazide (LHMDS), potassium diisopropylamide (KDA), and butyl lithium (BuLi).

According to the method for producing N-pyranosyl-tryptophan of the present invention, preferably, the acid is selected from the group consisting of hydrochloric acid, sulfuric acid, nitric acid, phosphoric acid, p-toluenesulfonic acid, and 10-camphorsulfonic acid.

According to the method for producing N-pyranosyl-tryptophan of the present invention, preferably, the hydrogenation catalyst is selected from the group consisting of a palladium catalyst, a rhodium catalyst, a ruthenium catalyst, and platinum catalyst.

According to the method for producing N-pyranosyl-tryptophan of the present invention, preferably, the second base is selected from the group consisting of lithium hydroxide, sodium hydroxide, potassium hydroxide, and barium hydroxide.

According to the method for producing N-pyranosyl-tryptophan of the present invention, preferably, the hydroxyl-protecting group is selected from the group consisting of a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group.

According to the method for producing N-pyranosyl-tryptophan of the present invention, preferably, $R_1$ represents a methyl group, $R_2$ represents a propyl group, and $R_3$ represents a methyl group.

Another aspect of the present invention provides a method for producing a 1-pyranosyl-3-pyrazyl-indole compound used for producing N-pyranosyl-tryptophan comprising:

a step of allowing a pyranose compound represented by the formula (1):

(1)

wherein X each independently represent a hydroxyl-protecting group, to react with a 3-pyrazyl-indole compound represented by the formula (2):

(2)

wherein $R_1$, $R_2$, and $R_3$ each independently represent an alkyl group having 1 to 6 carbon atoms, in the presence of a first base to obtain a 1-pyranosyl-3-pyrazyl-indole compound represented by the formula (3):

(3)

wherein X each independently represent a hydroxyl-protecting group; and $R_1$, $R_2$, and $R_3$ each independently represent an alkyl group having 1 to 6 carbon atoms.

According to the method for producing a 1-pyranosyl-3-pyrazyl-indole compound, preferably, the combination of the pyranose and the pyranosyl is selected from the group consisting of a combination of α-mannose and α-mannosyl, a combination of β-mannose and β-mannosyl, a combination of α-glucose and α-glucosyl, and a combination of β-glucose and β-glucosyl.

According to the method for producing a 1-pyranosyl-3-pyrazyl-indole compound, preferably, the first base is selected from the group consisting of potassium hexamethyldisilazide (KHMDS), lithium 2,2,6,6-tetramethyl piperizide (LiTMP), lithium diisopropylamide (LDA), lithium hexamethyldisilazide (LHMDS), potassium diisopropylamide (KDA), and butyl lithium (BuLi).

According to the method for producing a 1-pyranosyl-3-pyrazyl-indole compound, preferably, the hydroxyl-protecting group is selected from the group consisting of a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group.

According to the method for producing a 1-pyranosyl-3-pyrazyl-indole compound, preferably, $R_1$ represents a methyl group, $R_2$ represents a propyl group, and $R_3$ represents a methyl group.

Another aspect of the present invention provides an antibody against N-pyranosyl-tryptophan represented by the formula (4):

(4)

Another aspect of the present invention provides a method for producing an antibody against N-pyranosyl-tryptophan represented by the formula (4):

(4)

comprising a step of immunizing a mammalian animal with the N-pyranosyl-tryptophan, the N-pyranosyl-tryptophan having a protected amino group, or a conjugate comprising the N-pyranosyl-tryptophan or the N-pyranosyl-tryptophan having a protected amino group.

According to the method for producing an antibody against N-pyranosyl-tryptophan of the present invention, preferably, an amino group of N-pyranosyl-tryptophan is protected with the use of a protecting group selected from the group consisting of a fluorenylmethoxy group, a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group.

The present invention provides a method for producing a large amount of N-pyranosyl-tryptophan, such as N-glucosyl-tryptophan and N-mannosyl tryptophan, while its α-form and β-form at the anomeric positions are specified. Peptide extension via the addition of an amino acid to the N-glucosyl-tryptophan or N-mannosyl tryptophan obtained via synthesis enables comparative analysis with data of documents (e.g., Li et al., J. Biol. Chem., 2005, 280, 38513) or the like, which in turn enables identification of the presence of either the α-form or β-form in vivo. According to the present invention, further, an antibody can be produced from the produced N-pyranosyl-tryptophan, such as N-glucosyl-tryptophan or N-mannosyl tryptophan. Such antibody is an useful tool for an important discovery in order to learn the distribution patterns, biological functions, and the like of N-pyranosyl-tryptophan in vivo in, for example, plants or mammalian animals. Further, analysis of dynamics of N-pyranosyl-tryptophan in vivo can lead to development of a method for diagnosing diseases associated with N-pyranosyl-tryptophan and drugs for such diseases.

DETAILED DESCRIPTION OF THE INVENTION

Hereafter, embodiments of the present invention are described in detail.

The method for producing N-pyranosyl-tryptophan of the present invention comprises a step of allowing a pyranose compound to react with a 3-pyrazyl-indole compound in the presence of a first base to obtain a 1-pyranosyl-3-pyrazyl-indole compound; and a step of treating the 1-pyranosyl-3-pyrazyl-indole compound with an acid, treating the resultant with a hydrogenation catalyst, and further treating the resultant with a second base to obtain N-pyranosyl-tryptophan.

The method for producing a 1-pyranosyl-3-pyrazyl-indole compound used for producing N-pyranosyl-tryptophan of the present invention comprises a step of allowing a pyranose compound to react with a 3-pyrazyl-indole compound in the presence of the first base to obtain a 1-pyranosyl-3-pyrazyl-indole compound.

The term "pyranose compound" used herein refers to a compound represented by the formula (1):

(1)

wherein X each independently represent a hydroxyl-protecting group. The basic skeleton of the pyranose compound is not particularly limited, provided that a pyranose compound represented by the formula (1) can be constructed. Examples thereof include α-mannose, β-mannose, α-glucose, and β-glucose.

The term "hydroxyl-protecting group" used herein is not particularly limited, provided that such group can protect hydroxyl groups bound to carbon atoms at positions 3, 4, and 6 of the pyranose compound. Examples thereof include a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group, with a benzyl group being preferable. Further, the expression "X each independently represent a hydroxyl-protecting group" used herein means that protecting groups of hydroxyls bound to carbon atoms at positions 3, 4, and 6 of the pyranose compound are each independently one of the hydroxyl-protecting groups described above. Protecting groups of hydroxyls bound to carbon atoms at positions 3, 4, and 6 of the pyranose compound may each independently be a different protecting group, or may all be the same.

A method for producing a pyranose compound is not particularly limited, provided that a pyranose compound represented by the formula (1) can be constructed. For example, a pyranose compound can be produced via a known organic synthesis method comprising a step of forming an epoxide between carbon atoms at position 1 and at position 2 of α-mannose, β-mannose, α-glucose, or β-glucose and a step of protecting a hydroxyl group bound to a carbon atom at position 3, 4, or 6.

The term "3-pyrazyl-indole compound" used herein refers to a compound represented by the formula (2):

(2)

wherein $R_1$, $R_2$, and $R_3$ each independently represent an alkyl group having 1 to 6 carbon atoms.

The term "alkyl group" used herein refers to, for example, an alkyl group having 1 to 6 carbon atoms, and it may be linear or branched. Specific examples include a methyl group, an ethyl group, a propyl group, a butyl group, a pentyl group, and a hexyl group. Further, the expression "$R_1$, $R_2$, and $R_3$ each independently represent an alkyl group having 1 to 6 carbon atoms" used herein means that each of $R_1$, $R_2$, and $R_3$ separately represents an alkyl group having 1 to 6 carbon atoms. Accordingly, $R_1$, $R_2$, and $R_3$ may each represent a different alkyl group or may all be the same alkyl group.

A 3-pyrazyl-indole compound can be represented by a formula, such as the formula (2). A specific example of a 3-pyrazyl-indole compound is a 3-pyrazyl-indole compound in which $R_1$ represents a methyl group, $R_2$ represents a propyl group, and $R_3$ represents a methyl group.

A method for producing a 3-pyrazyl-indole compound is not particularly limited, provided that a compound represented by the formula (2) can be constructed. For example, such compound can be produced by allowing (R)-2,5-dihydro-3,6-dimethoxy-2-isopropylpyrazine to react with indole bromide, as described in the examples below.

The expression "allowing . . . to react . . . in the presence of a first base" used herein means that a base is added dropwise to a solution of a 3-pyrazyl-indole compound dissolved in a solvent, and a pyranose compound is further added to perform the reaction, as described in the examples below, for example.

Examples of the first base include: organic bases, such as amine and pyridine; salts of alkali metals, such as organic acid salt, carbonate, hydrogencarbonate, phosphate, and sulfite of alkali metals; salts of alkaline earth metals, such as organic acid salt, carbonate, hydrogencarbonate, phosphate, and sulfite of alkaline earth metals; inorganic bases, such as hydroxides and oxides of alkali metals, and hydroxides and oxides of alkaline earth metals. Specific examples of such first bases that can be used include potassium hexamethyldisilazide (KHMDS), lithium 2,2,6,6-tetramethyl piperizide (LiTMP), lithium diisopropylamide (LDA), lithium hexamethyldisilazide (LHMDS), and potassium diisopropylamide (KDA). Preferably, potassium hexamethyldisilazide (KHMDS) or butyl lithium (BuLi) can be used.

The amount of the first base to be used is not particularly limited, provided that it is active in the reaction. The amount is 1 to 10 moles, and preferably 3 to 5 moles, per mole of a 3-pyrazyl-indole compound. The amounts of the pyranose compound and the 3-pyrazyl-indole compound to be used are as follows. The amount of the 3-pyrazyl-indole compound is 1 to 10 moles, preferably 1 to 5 moles, and more preferably 1 to 3 moles, per mole of the pyranose compound.

A solvent used in the reaction is not particularly limited, provided that it is inactive in the reaction. Examples thereof include: aromatics, such as benzene, toluene, xylene, and chlorobenzene; ethers, such as diethyl ether, dibutyl ether, tetrahydrofuran, 1,4-dioxane, dimethoxyethane, and diethylene glycol dimethyl ether; esters, such as methyl acetate, ethyl acetate, butyl acetate, and ethyl propionate; ketones, such as acetone, methyl ethyl ketone, methyl isobutyl ketone, and cyclohexane; hydrocarbons, such as hexane, heptane, octane, and nonane; halogenated hydrocarbons, such as dichloromethane, chloroform, and 1,2-dichloroethane; organic acids, such as formic acid, acetic acid, and propionic acid; polar solvents, such as N,N-dimethylformamide, N,N-dimethylacetamide, and N-methylpyrrolidone; and water. A mixed solvent of any thereof can also be used. The amount of a solvent to be used is 1 to 50 times, and preferably 10 to 30 times, greater than that of the 3-pyrazyl-indole compound.

The reaction temperature is generally from the melting point to the boiling point of the reaction solvent, preferably from 0° C. to the boiling point of the reaction solvent, and more preferably from 0° C. to room temperature. The duration of the reaction is 0.5 to 48 hours, and preferably 0.5 to 24 hours.

The term "1-pyranosyl-3-pyrazyl-indole compound" used herein refers to a compound represented by the formula (3):

(3)

wherein X each independently represent a hydroxyl-protecting group; and $R_1$, $R_2$, and $R_3$ each independently represent an alkyl group having 1 to 6 carbon atoms. The 1-pyranosyl-3-pyrazyl-indole compound can be obtained by allowing the pyranose compound to react with the 3-pyrazyl-indole compound in the presence of a base.

The expression "treating the 1-pyranosyl-3-pyrazyl-indole compound with an acid, treating the resultant with a hydrogenation catalyst, and further treating the resultant with a second base" used herein means that an acid is added to a solution of the 1-pyranosyl-3-pyrazyl-indole compound dissolved in a solvent to perform the reaction, a hydrogenation catalyst is added to the resulting solution to perform the reaction, and then the second base is further added to the above solution to perform the reaction.

A solvent to be used in the reaction is not particularly limited, provided that it is inactive in the reaction. Examples thereof include: aromatics, such as benzene, toluene, xylene, and chlorobenzene; ethers, such as diethyl ether, dibutyl ether, tetrahydrofuran, 1,4-dioxane, dimethoxyethane, and diethylene glycol dimethyl ether; esters, such as methyl acetate, ethyl acetate, butyl acetate, and ethyl propionate; ketones, such as acetone, methyl ethyl ketone, methyl isobutyl ketone, and cyclohexanone; hydrocarbons, such as hexane, heptane, octane, and nonane; halogenated hydrocarbons, such as dichloromethane, chloroform, and 1,2-dichloroethane; organic acids, such as formic acid, acetic acid, and propionic acid; polar solvents, such as N,N-dimethylformamide, N,N-dimethylacetamide, and N-methylpyrrolidone; and water. A mixed solvent of any thereof can also be used. The amount of the solvent to be used is 1 to 50 times, and preferably 10 to 30 times, greater than that of the 1-pyranosyl-3-pyrazyl-indole compound.

Examples of the acid that can be used include hydrochloric acid, sulfuric acid, nitric acid, phosphoric acid, p-toluenesulfonic acid, and 10-camphorsulfonic acid, with hydrochloric acid being preferable.

The amount of an acid to be used is 0.001 to 0.1 moles, and preferably 0.005 to 0.05 moles, per mole of the 1-pyranosyl-3-pyrazyl-indole compound.

Examples of a hydrogenation catalyst that can be used include transition metal catalysts, such as palladium, platinum, rhodium, and ruthenium catalysts and oxides thereof. Pd/C, Pd black, Pd/Al$_2$O$_3$, and Pd (OH)$_2$/C can be preferably used.

Examples of the second base that can be used include bases of lithium, sodium, potassium, and barium. Also, lithium hydroxide, sodium hydroxide, and potassium hydroxide can be preferably used.

The amounts of the hydrogenation catalyst and the second base to be used are 0.1 to 10 moles, and preferably 0.2 to 5 moles, per mole of the N-mannosyl tryptophan hydrochloric acid compound.

The reaction temperature is generally from the melting point to the boiling point of the reaction solvent, preferably from 0° C. to the boiling point of the reaction solvent, and more preferably from room temperature to the boiling point of the reaction solvent. The duration of the reaction is 0.5 to 48 hours, and preferably 0.5 to 24 hours.

The term "N-pyranosyl-tryptophan" used herein refers to a compound represented by the formula (4).

(4)

N-pyranosyl-tryptophan can be obtained by treating the 1-pyranosyl-3-pyrazyl-indole compound with hydrochloric acid and then treating the resultant with two or more metal catalysts. The "pyranosyl" used herein is determined in accordance with a pyranose compound to be used for synthesis. Examples thereof include α-mannosyl, β-mannosyl, α-glucosyl, and β-glucosyl.

The antibody of the present invention recognizes N-pyranosyl-tryptophan represented by the formula (4).

(4)

The antibody of the present invention is not particularly limited, provided that it binds specifically to the N-pyranosyl-tryptophan, and it may be a polyclonal or monoclonal antibody. The antibody of the present invention can be produced using N-pyranosyl-tryptophan as an antigen in accordance with a known method for producing an antibody or antiserum.

The method for producing the antibody against N-pyranosyl-tryptophan represented by the formula (4) comprises a step of immunizing a mammalian animal with the N-pyranosyl-tryptophan; the N-pyranosyl-tryptophan having a protected amino group; or a conjugate comprising the N-pyranosyl-tryptophan or the N-pyranosyl-tryptophan having a protected amino group.

(4)

Hereafter, methods for producing monoclonal and polyclonal antibodies against the N-pyranosyl-tryptophan are exemplified.

[Production of Monoclonal Antibody]

(a) Production of Monoclonal Antibody-Producing Cell

N-pyranosyl-tryptophan is administered to a mammalian animal at a site at which antibody production is possible via administration thereof alone or together with a carrier or diluent. In order to enhance the capacity for antibody production, a complete Freund's adjuvant or incomplete Freund's adjuvant may be administered at the time of administration. In general, administration is carried out once every 2 to 6 weeks and it is carried out approximately 2 to 10 times in total. Examples of mammalian animals that can be used include monkeys, rabbits, dogs, guinea pigs, mice, rats, sheep, and goats, with mice and rats being preferable.

From among mammalian animals immunized with an antigen, such as mice, for example, individuals in which the antibody titer has been observed are selected, spleen cells or lymph nodes are sampled 2 to 5 days after the final immunization, and antibody-producing cells contained therein are fused to myeloma cells obtained from allogeneic or heterogeneic animals to produce monoclonal antibody-producing hybridomas. An antibody titer in the antiserum can be assayed by, for example, allowing the labeled N-pyranosyl-tryptophan described below to react with the antiserum and then assaying activity of the labeling agent bound to the antibody. Fusion can be carried out by a known technique, such as Kohler and Milstein's method (Nature, 256, 495, 1975). Examples of fusion accelerators include polyethylene glycol (PEG) and Sendai virus, with PEG being preferable.

Examples of myeloma cells include mammalian myeloma cells, such as X63-Ag8-6.5.3, NS-1, P3U1, SP2/0, and AP-1, with X63-Ag8-6.5.3 being preferable. The ratio of the number of antibody-producing cells (spleen cells) to that of myeloma cells to be used is preferably about 1:1 to 20:1. Cell fusion can be efficiently performed by adding PEG (preferably PEG 1000 to PEG 6000) at a concentration of about 10% to 80% and performing incubation at 20 to 40° C., and preferably at 30 to 37° C., for 1 to 10 minutes.

Monoclonal antibody-producing hybridomas can be screened for by, for example, a method comprising the steps of adding a hybridoma culture supernatant to a solid phase (e.g., a microplate) to which antigens have adsorbed directly or together with carriers, adding anti-immunoglobulin antibodies (with anti-mouse immunoglobulin antibodies being used when mouse-derived cells are used for cell fusion) labeled with radioactive substances or enzymes, or protein A, and detecting monoclonal antibodies bound to the solid phase; or a method comprising the steps of adding a hybridoma culture supernatant to a solid phase to which anti-immunoglobulin antibodies or protein A have been adsorbed, and adding N-pyranosyl-tryptophan labeled with a radioactive substance or enzyme thereto, and then detecting monoclonal antibodies bound to the solid phase.

Monoclonal antibodies can be selected via a known technique or a technique in accordance therewith. Monoclonal antibodies can be generally selected by using a medium for animal cell culture to which HAT (hypoxanthine, aminopterin, and thymidine) has been added. Monoclonal antibodies can be selected and grown in any medium, provided that hybridomas can be grown therein. Examples of such medium that can be used include RPMI 1640 medium containing 1% to 20%, and preferably 10% to 20%, fetal calf serum, GIT medium containing 1% to 10% fetal calf serum (Wako Pure Chemical Industries, Ltd.), and serum-free medium for hybridoma culture (SFM-101; Nissui Pharmaceutical Co., Ltd.). Culture is generally conducted at 20 to 40° C., and preferably at approximately 37° C. The duration of culture is generally 5 days to 3 weeks, and preferably 1 week to 2 weeks. Culture can be generally carried out in the presence of 5% carbon dioxide. The antibody titer of the hybridoma culture supernatant can be assayed in the same manner as in the case of the assay of the antibody titer in the antiserum.

The thus-obtained monoclonal antibodies can be separated and purified by a known method, such as a method for separation and purification of immunoglobulin (e.g., salting out, alcohol precipitation, isoelectric precipitation, electrophoresis, adsorption/desorption with the use of an ion exchanger (e.g., DEAE), ultracentrifugation, gel filtration, or specific purification wherein antibodies are selectively sampled with the use of an antigen-bound solid phase or an active adsorbent, such as protein A or G, and a bond is dissociated to obtain antibodies).

[Preparation of Polyclonal Antibody]

Polyclonal antibodies against N-pyranosyl-tryptophan can be produced in accordance with a known method. For example, immunogens (i.e., N-pyranosyl-tryptophan) by themselves or conjugates thereof with carrier proteins are prepared, mammalian animals are immunized in the same manner as in the case of the method for producing monoclonal antibodies, anti-N-pyranosyl-tryptophan antibody-containing compounds are sampled from the immunized animals, and antibodies may then be separated and purified. Thus, polyclonal antibodies of interest can be produced.

Regarding conjugates of immunogens with carrier proteins used for immunizing mammalian animals, any type of carrier proteins can be used, and carriers can be crosslinked to haptens at any mixing ratio, provided that antibodies can efficiently react with the immunized haptens. For example, approximately 0.1% to 20%, and preferably about 1% to 5%, bovine serum albumin, bovine cycloglobulin, hemocyanin, or the like may be coupled to 1% by weight of hapten.

Haptens are coupled to carriers using a variety of condensing agents, such as glutaraldehyde, carbodiimide, maleimide-activating ester, active ester reagents containing a thiol group or dithiopyridyl group.

A condensation product is administered to a mammalian animal at a site at which antibody production can be carried out alone or in combination with a carrier or diluent. In order to enhance the capacity for antibody production, a complete Freund's adjuvant or incomplete Freund's adjuvant may be administered at the time of administration. In general, administration is carried out once every 2 to 6 weeks and it is carried out approximately 3 to 10 times in total.

Polyclonal antibodies can be sampled from the blood, ascites, or the like of the mammalian animal that has been immunized in the above-described manner. Sampling from the blood is preferable.

The polyclonal antibody titer in the antiserum can be assayed in the same manner as in the case of the assay of the antibody titer in the antiserum described above. Polyclonal antibodies can be separated and purified in accordance with a method for separation and purification of immunoglobulin that is similar to the above method for separation and purification of monoclonal antibodies.

The anti-N-pyranosyl-tryptophan antibodies enables assay of the amount of N-pyranosyl-tryptophan or a salt thereof in humans or other warm-blooded animals (e.g., rats, mice, guinea pigs, rabbits, sheep, goats, pigs, cows, horses, cats, dogs, monkeys, chimpanzees, or birds).

A specific method for producing the antibody against N-pyranosyl-tryptophan of the present invention can comprise a step of protecting an amino group of N-pyranosyl-tryptophan to obtain the protected N-pyranosyl-tryptophan, a step of bringing the resulting protected N-pyranosyl-tryptophan into contact with a conjugate material to obtain a (protected N-pyranosyl-tryptophan) conjugate, and a step of immunizing a mammalian animal with the resulting (protected N-pyranosyl-tryptophan) conjugate, when, for example, polyclonal antibodies against N-pyranosyl-tryptophan are to be produced.

Further, a specific method for producing the antibody against N-pyranosyl-tryptophan of the present invention can comprise a step of fusing spleen cells of a mammalian animal immunized with the (protected N-pyranosyl-tryptophan) conjugate to myeloma cells of a heterogeneous mammalian animal to obtain a fused cell mass and a step of immunochemically selecting cells that produce antibodies against the (protected N-pyranosyl-tryptophan) conjugate from among the resulting fused cell mass and cloning the same, in addition to the above steps, when producing, for example, a monoclonal antibody against N-pyranosyl-tryptophan.

An amino group of N-pyranosyl-tryptophan can be protected with the use of a protecting group without any particular limitation, provided that an amino group can be protected. For example, a protecting group such as a fluorenylmethoxy group, a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, or a tert-butyldiphenylsilyl group can be used. Use of a fluorenylmethoxy group is preferable, and use of a 9-fluorenylmethoxy group is more preferable. Accordingly, the term "protected N-pyranosyl-tryptophan" refers to N-pyranosyl-tryptophan having a protected amino group.

Materials for the above-mentioned conjugate are not particularly limited, provided that such materials would form a conjugate with the protected N-pyranosyl-tryptophan. Examples thereof include a protein or organic polymer, preferably a protein, and more preferably keyhole limpet hemocyanin (KLH) or bovine serum albumin (BSA).

A mammalian animal can be immunized with the (protected N-pyranosyl-tryptophan) conjugate by, for example, administering the (protected N-pyranosyl-tryptophan) conjugate to a rabbit several times, as described in the examples.

The step of fusing spleen cells of a mammalian animal immunized with the (protected N-pyranosyl-tryptophan) conjugate to myeloma cells of a heterogeneous mammalian animal to obtain a fused cell mass can be successfully carried out by, for example, fusing spleen cells of a rabbit immunized with the (protected N-pyranosyl-tryptophan) conjugate to myeloma cells of a mice which is a mammalian animal heterogeneous to a rabbit to obtain the fused cell mass, as described in the examples.

The step of immunochemically selecting cells that produce antibodies against the (protected N-pyranosyl-tryptophan) conjugate from among the resulting fused cell mass and cloning the same can be successfully carried out by, for example, selecting the cells via an ELISA method and cloning the cells via limiting dilution, as described in the Examples.

The present invention is described in greater detail with reference to the following examples, although the present invention is not limited thereto.

EXAMPLES

Example 1

Synthesis of α-N-Man-Trp (1) Organic Synthesis of Intermediate 3-Pyrazyl-Indole Compound

To a solution of (R)-2,5-dihydro-3,6-dimethoxy-2-isopropylpyrazine (Compound 3 in FIG. 1; 3.0 g, 16.3 mmol) in tetrahydrofuran (THF; 100 ml) and butyl lithium (BuLi; 1.60 M), a hexane (hexane) solution was added in an argon atmosphere at −78° C. After the mixture was stirred for 40 minutes, indole bromide (Compound 2 in FIG. 1; 5.65 g, 16.1 mmol) in 30 ml of THF was transferred via cannula. The flask was washed with 10 ml of THF. The mixture was stirred at −78° C. overnight, and the reaction was then terminated with a saturated ammonium chloride ($NH_4Cl$) solution. An aqueous phase was extracted with ethyl acetate (EtOAc). The mixed phase was washed with an aqueous solution of a salt of saturated sodium bicarbonate ($NaHCO_3$). The mixed phase was dried over sodium sulfate ($Na_2SO_4$), followed by filtration and evaporation. The residue was purified via silica gel chromatography (hexane:EtOAc=4:1 to 7:3) to obtain 4.73 g of an intermediate sulfonamide 3-pyrazyl-indole compound as a colorless oil.

Intermediate Sulfonamide 3-Pyrazyl-Indole Compound
$^1$H-NMR δ 7.91 (d, J=8.3 Hz, 1H), 7.78 (d, J=7.8 Hz, 2H), 7.51 (d, J=7.8 Hz, 1H), 7.48 (d, J=7.3 Hz, 1H), 7.39 (t, J=8.3 Hz, 2H), 7.20 (m, 2H), 7.17 (t, J=8.3 Hz, 2H), 4.30 (dd, J=8.4 Hz, 4.4 Hz, 1H), 3.64 (s, 3H), 3.63 (s, 3H), 3.17 (m, 3H), 2.07 (m, 1H), 0.86 (d, J=6.8 Hz, 3H), 0.58 (s, J=6.8 Hz, 3H); $^{13}$C-NMR δ 163.7 (C), 161.8 (C), 138.1 (C), 134.6 (C), 133.4 (CH), 131.4 (C), 129.0 (CH), 126.4 (CH), 124.3 (CH), 122.7 (CH), 119.9 (CH), 118.5 (C), 113.3 (CH), 60.4 (CH), 55.6 (CH), 52.4 ($CH_3$), 52.3 ($CH_3$), 31.5 (CH), 29.2 ($CH_2$), 19.1 ($CH_3$), 16.6 ($CH_3$); $[α]^{24}_D$−4.8 (c 0.5 $CHCl_3$).

Figure 1:
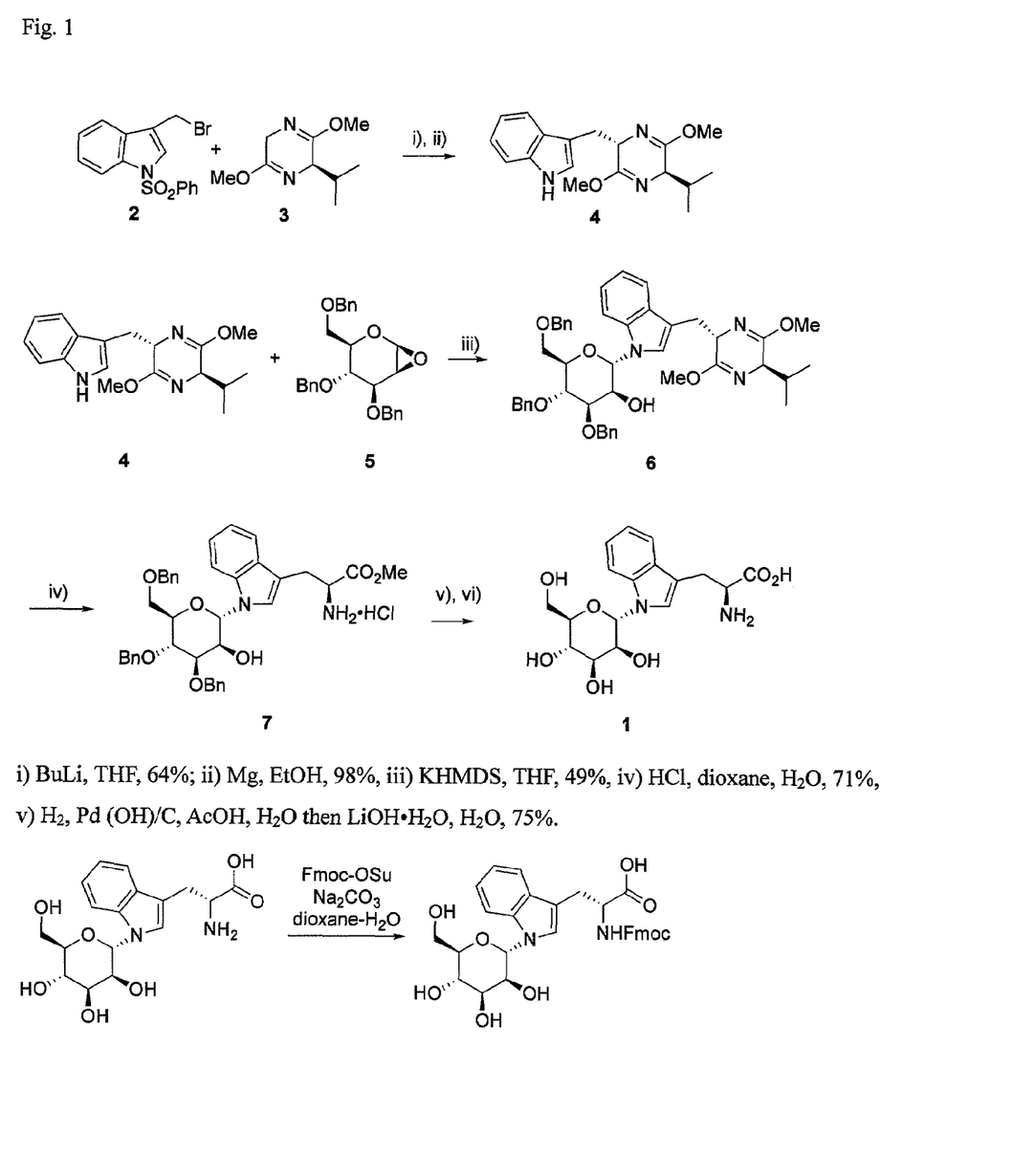
FIG. 1 shows a pathway for synthesizing a-N-mannosyl tryptophan.

(2) Organic Synthesis of 3-Pyrazyl-Indole Compound (Compound 4 in FIG. 1)

The intermediate sulfonamide 3-pyrazyl-indole compound (3.10 g, 6.84 mmol) and magnesium (1.50 g, 62.5 mmol) were stirred in 50 ml of methanol in a nitrogen atmosphere. After the exothermic reaction was terminated, a saturated $NH_4Cl$ solution was added. The aqueous phase was extracted with EtOAc. The mixed phase was washed with a salt solution and dried over $Na_2SO_4$. After filtration, the solvent was removed under reduced pressure. The residue was purified via silica gel chromatography (hexane:EtOAc=9:1 to 4:1) to obtain 2.10 g of a 3-pyrazyl-indole compound (98%).

3-Pyrazyl-Indole Compound
$^1$H NMR δ 7.83 (bs, 1H), 7.51 (d, J=7.8 Hz, 1H), 7.17 (d, J=7.8 Hz, 1H), 7.00 (t, J=7.8 Hz, 1H), 6.93 (t, J=7.8 Hz, 1H), 6.78 (s, 1H), 4.21 (dd, J=8.3 Hz, 3.9 Hz, 1H), 3.55 (s, 3H), 3.52 (s, 3H), 3.22 (t, J=3.4 Hz, 1H), 3.16 (s, 1H), 3.15 (s, 1H), 2.00 (m, 1H), 0.79 (d, J=7.2 Hz, 3H), 0.48 (d, J=6.8 Hz, 3H); $^{13}$C NMR δ 163 5 (C), 162.7 (C), 135.6 (C), 128.2 (C), 122.6 (CH), 121.5 (CH), 119.3 (CH), 118.9 (CH), 111.6 (C), 110.6 (CH), 60.4 (CH), 56.8 (CH), 52.3 ($CH_3$), 52.2 ($CH_3$), 31.4 (CH), 29.6 ($CH_2$), 19.1 ($CH_3$), 16.6 ($CH_3$); $[α]^{24}_D$+32 (c 1.1 $CHCl_3$).

(3) Organic Synthesis of 1-Pyranosyl-3-Pyrazyl-Indole Compound (Compound 6 in FIG. 1)

To a solution of a 3-pyrazyl-indole compound (1.67 g, 2.99 mmol) in THF (30 ml), potassium hexamethyldisilazide (KH- MDS; 0.5 M, a toluene solution) was added dropwise in a nitrogen atmosphere at 0° C. After the mixture was stirred at 0° C. for 30 minutes, a pyranose compound (Compound 5 in FIG. 1; 1.67 g, 3.88 mmol) was added several separate times. After the mixture was stirred overnight, the mixture was diluted with a saturated $NH_4Cl$ and EtOAc solution. The aqueous phase was extracted with EtOAc. The mixed phase was washed with a saturated $NaHCO_3$ salt solution. The mixture was dried over $Na_2SO_4$, followed by filtration and concentration. The residue was purified via silica gel chromatography (toluene:EtOAc=4:1) to obtain 1.10 g (49%) of a 1-pyranosyl-3-pyrazyl-indole compound.

1-Pyranosyl-3-Pyrazyl-Indole Compound $^1$H NMR δ 7.58 (d, J=7.6 Hz, 1H), 7.53 (d, J=8.0 Hz, 1H), 7.36-7.22 (m, 16H), 7.15 (t, J=7.6 Hz, 1H), 7.09 (t, J=7.1 Hz, 1H), 6.79 (s, 1H), 4.78-4.70 (m, 3H), 4.62-4.57 (m, 2H), 4.49 (m, 1H), 4.45 (d, J=12.4 Hz, 11H), 4.30 (m, 1H), 4.13 (m, 1H), 4.01 (t, J=10.0 Hz, 1H), 3.78 (m, 1H), 3.65 (s, 3H), 3.57 (s, 3H), 3.40 (s, 1H), 3.25 (dd, J=14.0 Hz, 3.6 Hz, 1H), 3.12 (dd, J=6.0 Hz, 14.4 Hz, 1H), 2.73 (m, 1H), 2.05 (m, 1H), 0.90 (d, J=6.8 Hz, 3H), 0.59 (d, J=6.8 Hz, 3H); $^{13}$C NMR δ 137.9 (C), 137.8 (C), 137.2 (C), 136.4 (C), 129.1 (C), 128.6 (CH), 128.2 (CH), 128.2 (CH), 127.9 (CH), 127.7 (CH), 127.6 (CH), 127.5 (CH), 122.0 (CH), 119.7 (CH), 119.3 (CH), 111.1 (CH), 79.2 (CH), 77.2 (CH), 73.9 (CH), 73.6 ($CH_2$), 73.3 ($CH_2$), 73.0 ($CH_2$), 67.7 (CH), 60.4 (CH), 31.3 (CH), 19.1 ($CH_3$), 16.5 ($CH_3$); $[α]^{24}_D$+95 (c 1.5 $CHCl_3$).

(4) Organic Synthesis of N-Mannosyl Tryptophan Hydrochloric Acid Compound (Compound 7 in FIG. 1)

To a solution of a 1-pyranosyl-3-pyrazyl-indole compound (696 mg, 0.93 mmol) in dioxane-$H_2O$ (10 ml, 1:1), hydrochloric acid (a 4.0 M solution in dioxane, 2.5 ml) was added at room temperature, and the mixture was stirred for 30 minutes. The mixture was diluted with dioxane, and a solvent was then evaporated. The residue was purified via silica gel chromatography (AcOEt-AcOH:MeOH=20:1) to obtain an N-mannosyl tryptophan hydrochloric acid compound (450 mg, 71%).

N-Mannosyl-Tryptophan Hydrochloric Acid Compound $^1$H NMR ($CD_3OD$) δ 7.57 (m, 2H), 7.40-7.16 (m, 18H), 5.89 (d, J=8.0 Hz, 1H), 4.79 (d, J=11.2 Hz, 1H), 4.68-4.48 (m, 7H), 4.36 (m, 1H), 4.14-4.06 (m, 3H), 3.83 (s, 3H), 3.67 (m, 1H), 3.50 (dd, J=14.0 Hz, 3.6 Hz, 1H); $^{13}$C-NMR δ ($CD_3OD$) 170.3 (C), 139.0 (C), 138.3 (C), 129.4 (CH), 129.3 (CH), 129.3 (CH), 129.2 (CH), 129.0 (CH), 128.9 (CH), 128.8 (CH), 128.6 (CH), 126.2 (CH), 123.5 (CH), 121.4 (CH), 119.1 (CH), 112 3 (CH), 108.9 (C), 79.2 (CH), 77.1 (CH), 75.2 (CH), 74.5 ($CH_2$), 74.1 ($CH_2$), 73.4 ($CH_2$), 68.7 ($CH_2$), 67.8 (CH), 54.3 (CH), 53.8 (CH), 27.4 ($CH_2$); $[α]^{24}_D$+43 (c 0.35 $CH_3OH$).

(5) Organic Synthesis of α-N-Mannosyl Tryptophan (Compound 1 in FIG. 1)

A mixture of an N-mannosyl tryptophan hydrochloric acid compound (206 mg, 0.30 mmol) and 20% Pd $(OH)_2$/C (100 mg) was stirred in acetic acid (AcOH; 6 ml) and water (2 ml) in a hydrogen atmosphere at 50° C. overnight. The catalyst was filtered and then washed with water. After lyophilization, a crude product was dissolved in 1 ml of water, and a lithium hydroxide hydrate ($LiOH·H_2O$; 52 mg, 1.37 mmol) was added at room temperature. Two hours thereafter, the mixture was purified via reversed-phase column chromatography ($H_2O$—$H_2O$:MeOH=7:3) to obtain α-N-mannosyl tryptophan (68 mg, 75%).

α-N-Mannosyl Tryptophan $^1$H NMR $D_2O$ (600 MHz, $KH_2PO_4$—$Na_2HPO_4$ buffer pH 7, dioxane 3.75 ppm as a reference, 25° C.), 7.74 (d, J=8.1 Hz, 1H), 7.72 (d, J=8.1 Hz, 1H), 7.36 (dd, J=8.1 Hz, 7.1 Hz, 1H), 7.27 (dd, J=8.1 Hz, 7.1 Hz, 1H), 6.03 (d, J=4.5 Hz, 1H), 4.68 (dd, J=4.5 Hz, 3.5 Hz, 1H), 4.21 (dd, J=6.5 Hz, 3.5 Hz, 1H), 4.00 (dd, J=12.6 Hz, 7.6 Hz, 1H), 3.92 (dd, J=6.5 Hz, 6.5 Hz, 1H), 3.76 (ddd, J=7.6 Hz, 6.5 Hz, 3.0 Hz, 1H), 3.76 (dd, J=12.6 Hz, 3.0 Hz, 1H), $^{13}$C NMR δ 175.0 (C), 137.5 (C), 128.5 (C), 123.5 (CH), 125.8 (CH), 121.4 (CH), 119.6 (CH), 112.3 (CH), 110.2 (C), 82.4 (CH), 77.5 (CH), 71.8 (CH), 68.6 (CH), 28.2 (CH), 60.5 ($CH_2$), 55.4 (CH).

Example 2

Preparation of N-Man-Trp Antibody (1) Synthesis of Fmoc-α-N-Man-Trp

Fmoc-OSu (26 mg, 0.0792 mmol) and α-N-Man-Trp (10.0 mg, 0.0258 mmol) were dissolved in 0.5% $NaHCO_3$ (0.5 ml) and DME (0.5 ml), and the resultant was stirred at room temperature overnight. The pH level of the reaction solution was adjusted to 4 with the use of an aqueous solution of 1 M HCl, and the reaction solution was directly purified via reversed-phase silica gel chromatography ($H_2O$ only/$H_2O$-

MeOH 1:1/H₂O:MeOH 1:9) to obtain 13.5 mg (89%) of Fmoc-α-N-Man-Trp.

MS 611 (M+Na)

Fmoc-α-N-Man-Trp (2) Binding of Hapten with KLH or BSA

The hapten (Fmoc-α-N-Man-Trp) obtained in (1) above was bound to keyhole limpet hemocyanin (KLH) or bovine serum albumin (BSA) using the Imject Immunogen EDC Conjugation Kit (#77602; Pierce) in accordance with a conventional technique. Specifically, after KLH or BSA (2 mg/0.2 ml H₂O) and Fmoc-α-N-Man-Trp (2 mg/0.5 ml conjugation buffer containing 20% DMSO) were prepared, they were quickly mixed, and the mixture was then subjected to the reaction at room temperature for 2 hours. The Fmoc group was removed with the aid of 1M NaOH and neutralized with HCl. Desalting was carried out using the NAP-10 molecular sieve column (GE Biosciences), and the resultant was used as an antigen.

(3) Preparation of Polyclonal Antibody

A mixture comprising equivalent amounts of Freund's complete adjuvant (ICN Biochemicals Inc.) and α-N-Man-Trp-KLH was administered subcutaneously to dorsal sites of female rabbits (NZW) (Japan SLC, Inc.) at 0.5 mg/individual. Thereafter, a mixture comprising equivalent amounts of Freund's incomplete adjuvant (ICN Biochemicals Inc.) and α-N-Man-Trp-KLH was administered subcutaneously to dorsal sites of the rabbits twice at intervals of 3 weeks at 0.2 mg/individual. Three weeks thereafter, final immunization was carried out with a mixture containing the same antigen at 0.2 mg/individual, and the antiserum was prepared via whole blood collection 5 days later.

(4) Preparation of Monoclonal Antibody

A mixture comprising equivalent amounts of Freund's complete adjuvant (ICN Biochemicals Inc.) and α-N-Man-Trp-KLH was administered intraperitoneally to 8-week-old female Balb/c mice (Japan SLC, Inc.) at 0.2 mg/individual. Thereafter, a mixture comprising equivalent amounts of Freund's incomplete adjuvant (ICN Biochemicals Inc.) and α-N-Man-Trp-KLH was administered intraperitoneally to the mice twice at intervals of 3 weeks at 0.1 mg/individual. Three weeks thereafter, final immunization was carried out with a mixture containing the same antigen at 0.1 mg/individual, and antibody-producing cells were prepared from the spleens 3 days later. The spleens were aseptically extracted from the immunized mice under anesthesia, the tissue was loosed in serum-free RPMI-1640 medium (Sigma), spleen cells were unicellularized using a #100 stainless steel mesh, and the resultant was then washed three times with serum-free RPMI-1640 medium. Mouse myeloma cells, X63-Ag8-6.5.3 (obtained from the Health Science Research Resources Bank), were cultured in RPMI-1640 medium containing 20% fetal calf serum (abbreviated as "FCS"). The cells at the logarithmic growth phase were collected and washed three times with serum-free RPMI-1640 medium.

Antibody-producing cells were mixed with mouse myeloma cells, X63-Ag8-6.5.3, at a ratio of 5:1, and a culture solution was removed via centrifugation at 900 g for 5 minutes. A solution of 50% polyethylene glycol 1500 (1 ml, Sigma) was added to the cell deposits resulting from centrifugation, cell fusion was initiated, and 30 ml of serum-free RPMI-1640 medium was then added gradually. Thereafter, the culture solution was removed via centrifugation at 900 g for 5 minutes, and the cell deposit resulting from centrifugation was suspended in HAT medium (Sigma) to adjust the cell density to $1 \times 10^6$ cells/ml. The cell suspension was fractionated in amounts of 0.1 ml per well of a 96-well microplate. Thereafter, the cells were continuously cultured in a CO₂ incubator (37° C., 5% CO₂, 95% air). Ten days later, hybridoma colonies were observed in the wells.

(5) Screening Assay

Wells containing cells that produce target antibodies were selected in the following manner. A 96-well microplate was coated with α-N-Man-Trp-BSA (0.01 mg/ml of 100 mM sodium carbonate buffer) overnight at 4° C. to prepare an assay plate. α-N-Man-Trp-BSA was prepared in the manner described in (2) above. The assay plate was washed three times with a phosphate buffer (abbreviated as PBS), 0.1 ml of 1% bovine serum albumin (abbreviated as BSA)/PBS solution was fractionated to the wells, the reaction was conducted at room temperature for 1 hour, and the resultant was designated as a reaction plate. Each well was washed three times with PBS, 0.1 ml of the culture supernatant diluted to 2-fold with 0.5% BSA-containing PBS was introduced, and the reaction was conducted at room temperature for 2 hours. After the completion of the reaction, the plate was washed four times with PBS containing 0.05% Tween-20, 0.05 ml of peroxidase-labeled-antimouse immunoglobulins-rabbit IgG (DAKO) was added, and the reaction was conducted at room temperature for 1 hour. After the completion of the reaction, the plate was washed four times with PBS containing 0.05% Tween-20, 0.05 ml of a TMB One solution (Promega) was added, and the reaction was conducted at room temperature for 30 minutes. Finally, 0.05 ml of 2N HCl was added to terminate the reaction, and absorbance at 450 nm was assayed using a microplate reader (Biorad). The cells in the 4 wells that had tested positive in the end were subjected to cloning.

Also, the antibody titer of the rabbit antiserum was evaluated by the above assay technique.

(6) Cloning

Cloning was carried out via limiting dilution in accordance with a conventional technique. The cells that had tested positive were diluted to 10 cells/ml in 10% FCS-containing RPMI-1640 medium containing thymocytes at $1 \times 10^7$ cells/ml, the resultant was fractionated in amounts of 0.1 ml per well of the 96-well microplate, and culture was conducted in a CO₂ incubator (37° C., 5% CO₂, 95% air). The wells in which a grown colony was observed at 1 cell/well were selected 10 days after the initiation of culture, the culture supernatants of the selected wells were assayed and evaluated by the assay technique described above, and wells containing cell strains that produce target antibodies were selected.

(7) Evaluation of Antibody Titer with Regard to α-N-Man-Trp (Rabbit Antiserum)

Figure 2:
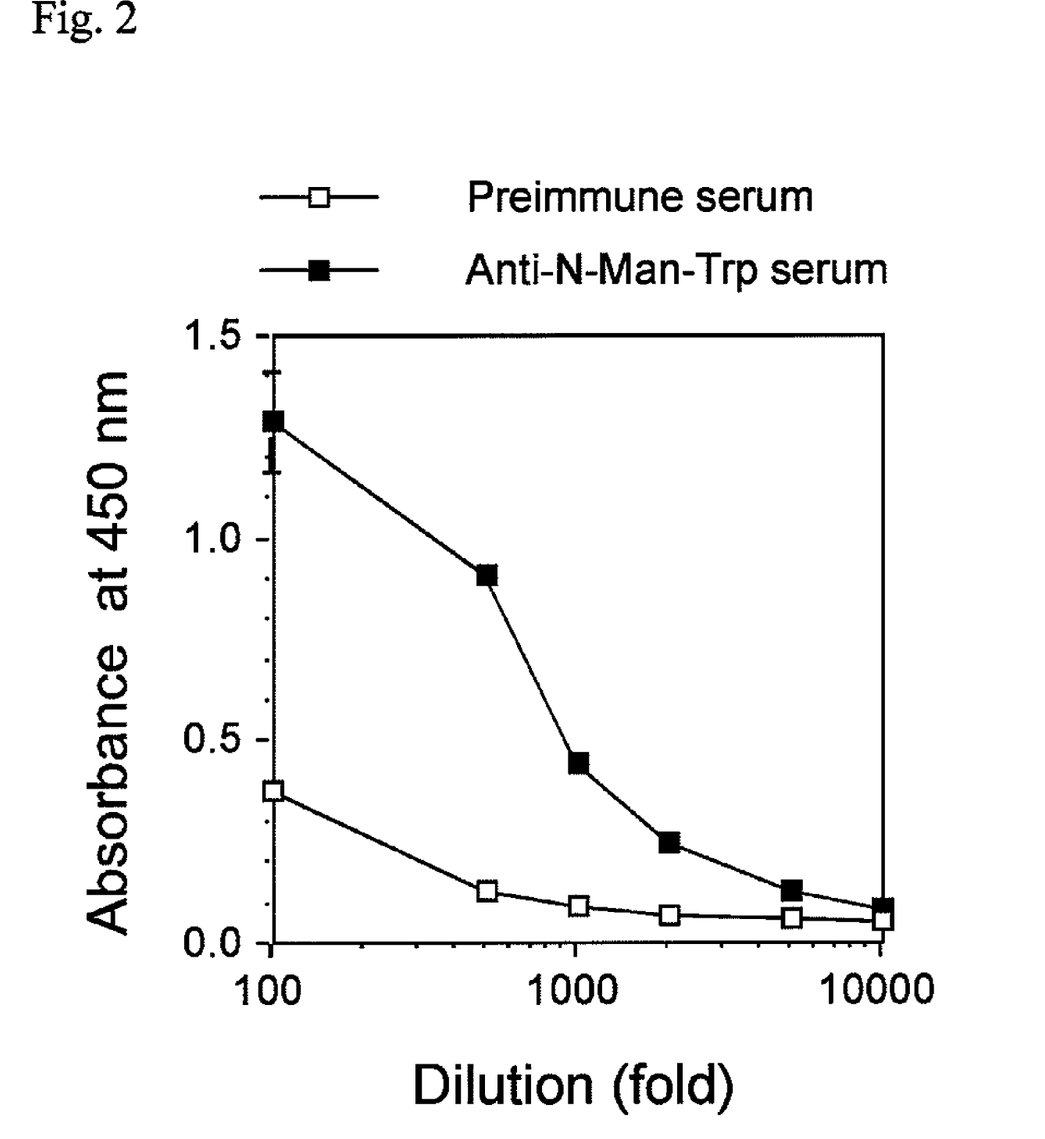
FIG. 2 shows the results of evaluation of an antibody titer against α-N-Man-Trp (rabbit antiserum).

A 96-well microplate was coated with α-N-Man-Trp-BSA (0.01 mg/ml of 100 mM sodium carbonate buffer) overnight at 4° C. to prepare an assay plate. The rabbit antiserum (0.1 ml) diluted with 0.5% BSA-containing PBS was introduced, and the reaction was carried out at room temperature for 2 hours. After the completion of the reaction, the plate was washed, 0.05 ml of peroxidase-labeled-antirabbit immunoglobulin-goat IgG (DAKO) was added, and the reaction was conducted at room temperature for 1 hour. After washing, 0.05 ml of a TMB One solution (Promega) was added, and the reaction was conducted at room temperature for 30 minutes. Finally, 0.05 ml of 2N HCl was added to terminate the reaction, and absorbance at 450 nm was assayed using a microplate reader. The results of the assay are shown in FIG. 2. As shown in FIG. 2, the anti-N-Man-Trp serum exhibited higher absorbance than that attained with the serum of a control sample before immunization. This indicates that it contains a great amount of antibodies against N-Man-Trp.

(8) Inhibition Experiment Using Antigen (Rabbit Antiserum)

Figure 3:
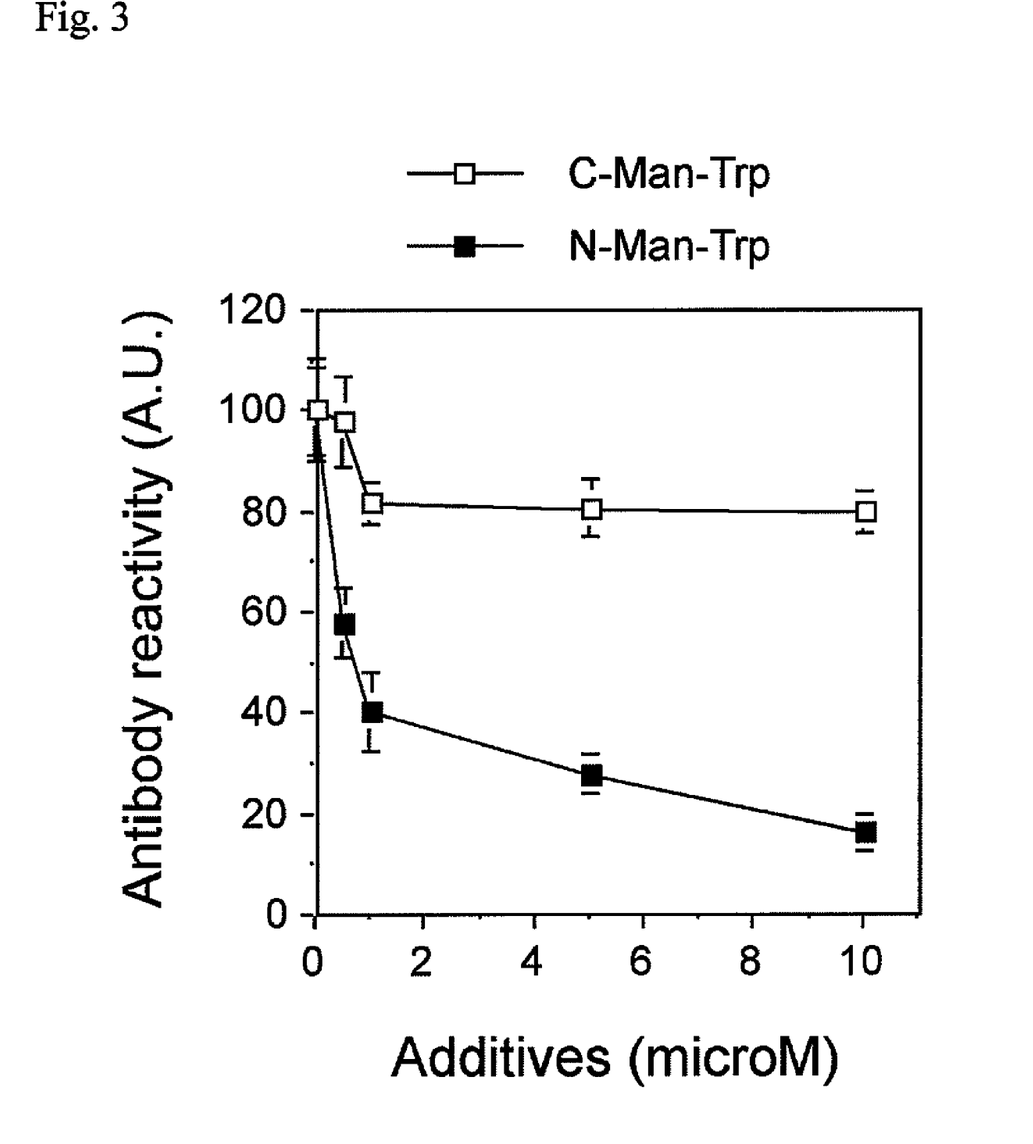
FIG. 3 shows the results of an inhibition experiment using an antigen (rabbit antiserum).

The assay plate coated with α-N-Man-Trp-BSA (0.01 mg/ml of 100 mM sodium carbonate buffer) was used, and ELISA using the anti-α-N-Man-Trp serum (2,000-fold diluted) was carried out in the manner described above. At the time of the addition of the anti-N-Man-Trp serum, α-N-Man-Trp or α-C-Man-Trp was allowed to be present at various concentrations in the solution, and the effects of inhibiting antiserum-antigen binding were evaluated. The results are shown in FIG. 3. As shown in FIG. 3, the anti-N-Man-Trp serum bound specifically to N-Man-Trp, and such binding was inhibited.

[Industrial Applicability]

The method for producing N-pyranosyl-tryptophan of the present invention enables mass-production of an α-form or β-form of N-pyranosyl-tryptophan having a specified structure and preparation of antibodies against N-pyranosyl-tryptophan.

What is claimed is:

1. A method for producing N-pyranosyl-tryptophan comprising:

a step of allowing a pyranose compound represented by the formula (1):

(1)

wherein X each independently represent a hydroxyl-protecting group, to react with a 3-pyrazyl-indole compound represented by the formula (2):

(2)

wherein $R_1$, $R_2$, and $R_3$ each independently represent an alkyl group having 1 to 6 carbon atoms, in the presence of a first base to obtain a 1-pyranosyl-3-pyrazyl-indole compound represented by the formula (3):

(3)

wherein X each independently represent a hydroxyl-protecting group; and $R_1$, $R_2$, and $R_3$ each independently represent an alkyl group having 1 to 6 carbon atoms; and a step of treating the 1-pyranosyl-3-pyrazyl-indole compound with an acid, treating the resultant with a hydrogenation catalyst, and further treating the resultant with a second base to obtain N-pyranosyl-tryptophan represented by the formula (4):

(4)

2. The method according to claim 1, wherein the pyranosyl group of the compound represented by the formula 3 or 4 is selected from the group consisting of α-mannosyl, β-mannosyl, α-glucosyl and β-glucosyl.

3. The method according to claim 1, wherein the first base is selected from the group consisting of potassium hexamethyldisilazide (KHMDS), lithium 2,2,6,6-tetramethyl piperizide (LiTMP), lithium diisopropylamide (LDA), lithium hexamethyldisilazide (LHMDS), potassium diisopropylamide (KDA), and butyl lithium (BuLi).

4. The method according to claim 1, wherein the acid is selected from the group consisting of hydrochloric acid, sulfuric acid, nitric acid, phosphoric acid, p-toluenesulfonic acid, and 10-camphorsulfonic acid.

5. The method according to claim 1, wherein the hydrogenation catalyst is selected from the group consisting of a palladium catalyst, a rhodium catalyst, a ruthenium catalyst, and platinum catalyst.

6. The method according to claim 1, wherein the second base is selected from the group consisting of lithium hydroxide, sodium hydroxide, potassium hydroxide, and barium hydroxide.

7. The method according to claim 1, wherein the hydroxyl-protecting group is selected from the group consisting of a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group.

8. The method according to claim 1, wherein $R_1$ represents a methyl group, $R_2$ represents a propyl group, and $R_3$ represents a methyl group.

9. A method for producing a 1-pyranosyl-3-pyrazyl-indole compound used for producing N-pyranosyl-tryptophan comprising:

a step of allowing a pyranose compound represented by the formula (1):

(1)

wherein X each independently represent a hydroxyl-protecting group, to react with a 3-pyrazyl-indole compound represented by the formula (2):

(2)

wherein $R_1$, $R_2$, and $R_3$ each independently represent an alkyl group having 1 to 6 carbon atoms, in the presence of a first base to obtain a 1-pyranosyl-3-pyrazyl-indole compound represented by the formula (3):

(3)

wherein X each independently represent a hydroxyl-protecting group; and $R_1$, $R_2$, and $R_3$ each independently represent an alkyl group having 1 to 6 carbon atoms.

10. The method according to claim 9, wherein the pyranosyl group of the compound represented by the formula 3 is selected from the group consisting of α-mannosyl, β-mannosyl, α-glucosyl, and β-glucosyl.

11. The method according to claim 9, wherein the first base is selected from the group consisting of potassium hexamethyldisilazide (KHMDS), lithium 2,2,6,6-tetramethyl piperizide (LiTMP), lithium diisopropylamide (LDA), lithium hexamethyldisilazide (LHMDS), potassium diisopropylamide (KDA), and butyl lithium (BuLi).

12. The method according to claim 9, wherein the hydroxyl-protecting group is selected from the group consisting of a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group.

13. The method according to claim 9, wherein $R_1$ represents a methyl group, $R_2$ represents a propyl group, and $R_3$ represents a methyl group.

14. A method for producing an antibody against N-pyranosyl-tryptophan represented by the formula (4):

(4)

Comprising:
i) producing N-pyranosyl-tryptophan comprising allowing a pyranose compound represented by the formula (1):

(1)

wherein X each independently represent a hydroxyl-protecting group, to react with a 3-pyrazyl-indole compound represented by the formula (2):

(2)

wherein $R_1$, $R_2$, and $R_3$ each independently represent an alkyl group having 1 to 6 carbon atoms, in the presence of a first base to obtain a 1-pyranosyl-3-pyrazyl-indole compound represented by the formula (3):

(3)

wherein X each independently represent a hydroxyl-protecting group; and $R_1$, $R_2$, and $R_3$ each independently represent an alkyl group having 1 to 6 carbon atoms; and treating the 1-pyranosyl-3-pyrazyl-indole compound with an acid, treating the resultant with a hydrogenation catalyst, and further treating the resultant with a second base to obtain N-pyranosyl-tryptophan represented by the formula (4):

(4)

(ii) immunizing a mammalian animal with the N-pyranosyl-tryptophan, the N-pyranosyl-tryptophan having a protected amino group, a conjugate comprising the N-pyranosyl-tryptophan or a conjugate comprising the N-pyranosyl-tryptophan having a protected amino group.

15. The method according to claim 14, wherein the pyranosyl group of the compound represented by the formula 3 or 4 is selected from the group consisting of α-mannosyl, β-mannosyl, α-glucosyl and β-glucosyl.

16. The method according to claim 14, wherein the first base is selected from the group consisting of potassium hexamethyldisilazide (KHMDS), lithium 2,2,6,6,-tetramethyl piperizide (LiTMP), lithium diisopropylamide (LDA), lithium hexamethyldisilazide (LHMDS), potassium diisopropylamide (KDA), and butyl lithium BuLi).

17. The method according to claim 14, wherein the acid is selected from the group consisting of hydrochloric acid, sulfuric acid, nitric acid, phosphoric acid, p-toluenesulfonic acid, and 10-camphorsulfonic acid.

18. The method according to claim 14, wherein the hydrogenation catalyst is selected from the group consisting of a palladium catalyst, a rhodium catalyst, a ruthenium catalyst, and platinum catalyst.

19. The method according to claim 14, wherein the second base is selected from the group consisting of lithium hydroxide, sodium hydroxide, potassium hydroxide, and barium hydroxide.

20. The method according to claim 14, wherein the hydroxyl-protecting group is selected from the group consisting of a benzyl group, a p-methoxybenzyl group, a tert-butyl group, a methoxymethyl group, a tetrahydropyranyl group, an ethoxyethyl group, an acetyl group, a pivaloyl group, a benzoyl group, a trimethylsilyl group, a triethylsilyl group, a tert-butyl dimethylsilyl group, a triisopropylsilyl group, a tert-butyldiphenylsilyl group, a trialkylsilyl group, a triarylsilyl group, and a tetrahydropyran ether group.

21. The method according to claim 14, wherein $R_1$ represents a methyl group, $R_2$ represents a propyl group, and $R_3$ represents a methyl group.

* * * * *